(12) United States Patent
Toro Restrepo et al.

(10) Patent No.: US 11,510,714 B2
(45) Date of Patent: Nov. 29, 2022

(54) STERNUM REPLACEMENT PLATE MADE IN ONE PIECE

(71) Applicant: TECHFIT DIGITAL SURGERY INC., Daytona Beach, FL (US)

(72) Inventors: Mauricio Toro Restrepo, Daytona Beach, FL (US); Juan Pablo Martínez Carett, Caldas Antioquia (CO); Daniel Restrepo Mejía, Medellín (CO)

(73) Assignee: TECHFIT DIGITAL SURGERY INC., Daytona Beach, FL (US)

( * ) Notice: Subject to any disclaimer, the term of this patent is extended or adjusted under 35 U.S.C. 154(b) by 0 days.

(21) Appl. No.: 16/877,559

(22) Filed: May 19, 2020

(65) Prior Publication Data

US 2021/0298808 A1 Sep. 30, 2021

(30) Foreign Application Priority Data

Mar. 30, 2020 (CO) .................. NC2020/0003879

(51) Int. Cl.
*A61B 17/80* (2006.01)
*A61B 17/82* (2006.01)

(52) U.S. Cl.
CPC ........ *A61B 17/8076* (2013.01); *A61B 17/823* (2013.01)

(58) Field of Classification Search
CPC .............. A61B 17/8076; A61B 17/823; A61B 17/8085; A61F 2002/30996
See application file for complete search history.

(56) References Cited

U.S. PATENT DOCUMENTS

| 2014/0257291 | A1* | 9/2014 | Houff | A61B 17/8076 606/284 |
| 2017/0360453 | A1* | 12/2017 | Brailovski | A61B 17/15 |
| 2018/0036052 | A1* | 2/2018 | Fabre | A61B 17/8023 |
| 2018/0177914 | A1 | 6/2018 | Setton et al. | |
| 2018/0193073 | A1* | 7/2018 | Frank | A61B 17/8076 |
| 2019/0374267 | A1* | 12/2019 | Madey | A61B 17/8076 |

(Continued)

FOREIGN PATENT DOCUMENTS

| CN | 109077831 A | 12/2018 |
| CN | 209136987 U | 7/2019 |

(Continued)

OTHER PUBLICATIONS

Hipolite, Whitney. "Woman with the Metal Chest: Surgeons Implant World's First 3D Printed Titanium Sternum—3dprint.Com: The Voice of 3D Printing / Additive Manufacturing." 3DPrint.Com., Jul. 9, 2015, https://3dprint.com/79908/3d-printed-sternum-implant/. (Year: 2015).*

*Primary Examiner* — Matthew J Lawson
(74) *Attorney, Agent, or Firm* — Schmeiser, Olsen & Watts, LLP

(57) ABSTRACT

Provided is an implant for sternum replacement including an upper face, a posterior face, extensions for fitting with the ribs and extensions for fitting with the manubrium, wherein that implant is manufactured in a single piece with high performance engineering polymers, with an anatomical adjustment tailored to each patient, which guarantees the reduction of the number of elements in contact with the patient, facilitating and speeding up the surgical procedure, at the same time, the required mechanical and flexibility properties, are guaranteed.

6 Claims, 2 Drawing Sheets

(56) References Cited

U.S. PATENT DOCUMENTS

Figure 1:
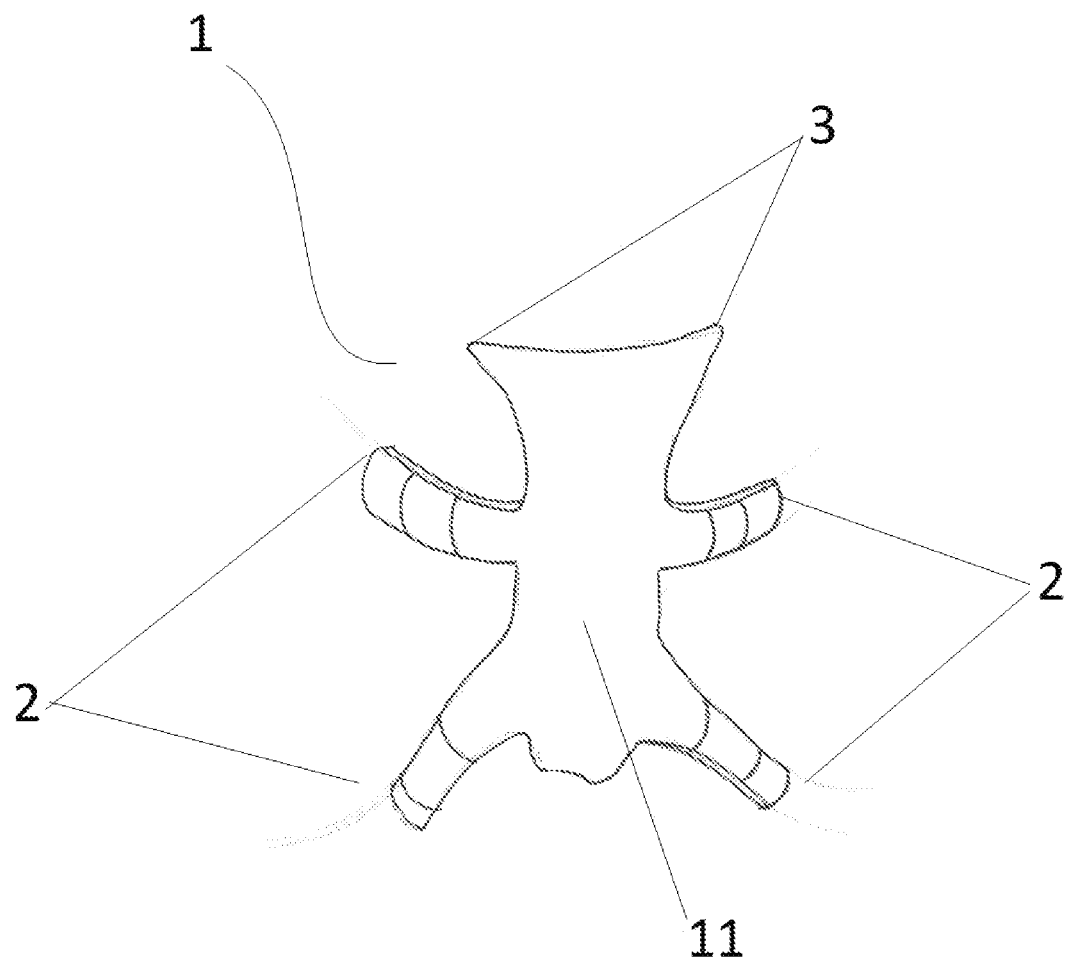

2020/0315675 A1\* 10/2020 Triana Espinel .... A61B 17/823
2020/0345399 A1\* 11/2020 Gregory, II ............ A61B 50/33

FOREIGN PATENT DOCUMENTS

| DE | 102019111978 A1 \* | 11/2020 |
| FR | 3032876 A1 | 2/2015 |
| WO | 2018/132179 A1 | 7/2018 |

\* cited by examiner

STERNUM REPLACEMENT PLATE MADE IN ONE PIECE

CROSS-REFERENCE TO RELATED APPLICATIONS

This application claims priority to Colombian Application No. NC2020/0003879, having a filing date of Mar. 30, 2020, the entire contents of which are hereby incorporated by reference.

FIELD OF TECHNOLOGY

The following relates to the field of biomedical engineering, particularly relates to an implant for sternum replacement comprising an upper face, a posterior face, extensions for fitting with the ribs and extensions for fitting with the manubrium, wherein that implant is manufactured in a single piece with high performance engineering polymers, with an anatomical adjustment tailored to each patient, which guarantees the reduction of the number of elements in contact with the patient, facilitating and speeding up the surgical procedure and, at the same time, providing the necessary mechanical and flexibility properties.

BACKGROUND

In some cases of infection, accidents, heart surgeries or the presence of cancer tumors, it is necessary to practice a total sternotomy, that is, the extraction of the sternum bone, which is a flat, odd, central and symmetrical (usually) chest bone, consisting of several welded parts. The sternum helps protect the heart and lungs. At the back of it is the mediastinum, which includes the extrapleural anatomical complement located in the center of the chest, between the left and right lungs.

To replace the sternum, a series of implants made with different materials have been used, among which the titanium metal plates, ceramic alumina plates, and in some cases in which the sternum is not completely replaced, high performance engineering polymers. However, normally this type of implant meets standard geometries and requires a large number of additional elements for fixation and complementary elements to guarantee the correct performance of the implant, hindering the surgical process and increasing the risk of infections and complications.

Thus, in the state of the art there are a plurality of disclosures related to implants or plates for total or partial sternum replacement, with different geometries and materials, among which is the document US2018177914, refers to an implant for sternum replacement comprising an alumina ceramic, where the alumina ceramic has a volume porosity of 45 to 75% and a pore size of 200 to 600 μm.

However, embodiments of the invention defined herein has the disadvantage that it is not custom made for the patient, at the same time it does not show an implant developed in high performance engineering polymers.

On the other hand, there is also document CN109077831A, in which provides a type of prosthetic sternum devices, which includes a sternal part; multiple rib cage portions located on the sternal side. The interior of one or more portions of the rib cage is disposed in the prosthetic fusion portion. Wherein said prosthetic fusion portion allows growth during the rib cage portion with the bone fusion to grow integrally, eventually grow to a relatively stable level and biologically active support construction, while this support construction may also cause stimulation transported to the peripheral blood, promoting the repair of damaged cartilage.

However, embodiments of the invention defined herein has the disadvantage that it is not custom made for the patient, at the same time it does not show an implant developed in high performance engineering polymers.

In the state of the art, there is also document WO2018/132179, which presents an implant for a human sternum and ribs that includes a sternal implant and a rib link. The sternal implant can be attached to the sternum. The rib bond may include a distal portion, a proximal portion, and a strut. The distal portion can be attachable to a rib. The proximal portion may be attachable to the sternal implant. The strut can connect the distal portion to the proximal portion. The strut can be configured to flex so that the distal portion can align with the rib.

However, embodiments of the invention defined herein has the disadvantage that it is not custom made for the patient in a single piece, at the same time it does not show an implant developed in high performance engineering polymers.

On the other hand, have document CN209136987U, which discloses a type of artificial sternum bone made of carbon/carbon composite material, including the main body of the sternum, and the integral structure of the branch is connected to the rib cage, and the connecting branch of the rib cage is distributed in the sternum on two sides. The artificial sternum bone has three layers, and the intermediate layer is a base layer of carbon/carbon composite material, and the upper epidermis is a coating High porosity carbon, and the layer is a pyrocarbon coating, a silicon carbide layer, or a pyrolytic carbon/silicon carbide mixed layer. Artificial sternum bone has many advantages, such as that light weight, specific resistance is high, histocompatibility is good, easy to use.

However, embodiments of the invention defined herein has the disadvantage that it is not custom made for the patient, at the same time it does not show an implant developed in high performance engineering polymers.

Finally, Document FR3032876A1 refers particularly to an implant for sternal closure after a sternotomy that is comprised of a central block comprised of a superior and an inferior face that comprises a first module and a second module. This first module is meant to be attached to one part of the sternum and has a medial face that is meant to be positions right in front of the medial side of the second module that is located in the other part of the sternum. Said implant has at least one means to join the two medial faces of the modules and at least one means of blocking the removable device that goes through at least one of the modules. Said means of blocking is accessible from the frontal side of the implant.

However, embodiments of the invention defined herein has the disadvantage that it is not custom made for the patient in a single piece.

In accordance with the previous statements, it is clear that in the state of the art there is a need to design an implant for sternum replacement tailored to the patient, which has a geometry that adjusts to the ribs, the mediastinum and the manubrium, that is developed in a single piece in a material that guarantees flexibility for its correct operation.

Additionally, it is necessary that those implants have properties of high resistance, light weight, biocompatibility, and that allow avoiding the risk of infections, facilitating and expediting surgical interventions.

BRIEF DESCRIPTION

Figure 2:
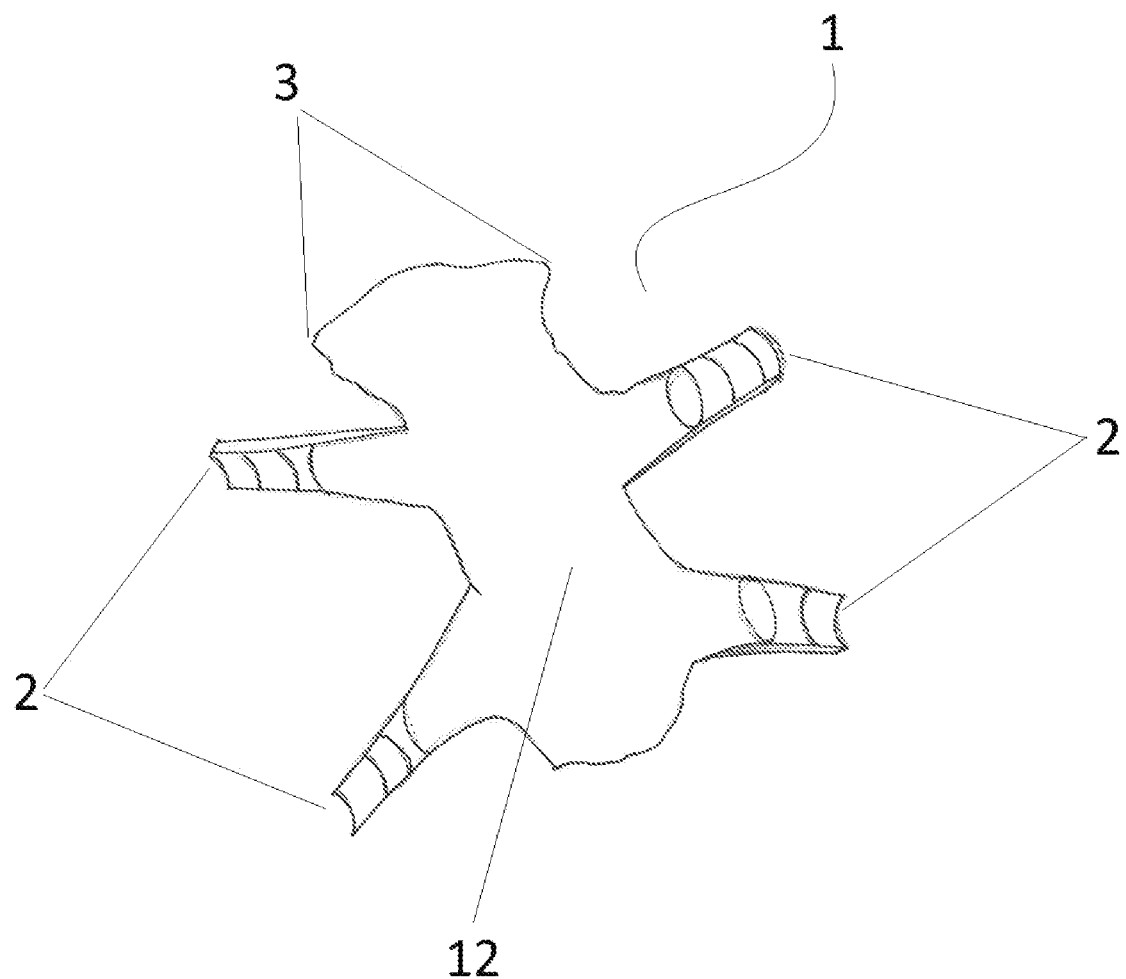

Some of the embodiments will be described in detail, with references to the following Figures, wherein like designations denote like members, wherein:

FIG. 1 corresponds to a front view of the implant for sternum replacement; and FIG. 2 corresponds to a posterior view of the implant for sternum replacement.

DETAILED DESCRIPTION

Embodiments of the present invention is directed to an implant for sternum replacement, which is composed of the following components:

Sternum implant (1) comprising an upper face (11), a posterior face (12), extensions for coupling with the ribs (2), extensions for coupling with the manubrium (3), wherein that implant is made from high performance engineering polymers, such as PEEK, PEKK or carbon fiber reinforced PEEK, where those fibers are continuous or discontinuous, in order to guarantee the necessary mechanical properties, at the same time as they are biocompatible, lightweight and highly resistant and flexible which facilitates the reduction of the number of pieces necessary for the intervention, also reducing the risk of infection.

This implant is manufactured in a single piece by machining, in accordance with CAD/CAM techniques and computer-assisted surgical planning, in order to adjust to the anatomy of each patient, specifically, the geometry of that posterior face fits anatomically with the mediastinum, the geometry of those fitting extensions with the ribs is anatomically adjusted with the ribs, the geometry of those fitting extensions with the manubrium is anatomically adjusted with the manubrium.

This implant is fixed to the patient's body, by direct fixation or through holes where titanium or steel screws are placed, or with titanium and steel plates.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements.

The invention claimed is:

1. A sternum implant comprising:
   a main body section;
   a top end of the main body section configured to be located at a manubrium when fixed to a body of a patient;
   a bottom end of the main body section, distal to the top end, wherein the main body section extends from the top end to the bottom end;
   an upper face;
   a posterior face;
   first extensions for fitting with ribs; and
   second extensions for fitting with the manubrium, the second extensions forming a shape of the top end;
   wherein the sternum implant is manufactured with engineered polymers;
   wherein the upper face, the posterior face, the first extensions, and the second extensions are structurally integral with the main body section as a function of the sternum implant being manufactured as a single piece;
   wherein the bottom end is free of extensions;
   wherein the sternum implant is configured to be fixed to a rib bone of a body of a patient with screws.

2. The sternum implant of claim 1, wherein the sternum implant is a sternum replacement implant.

3. The sternum implant according to claim 1, wherein:
   a geometry of the posterior face fits anatomically with a mediastinum,
   a geometry of the first extensions are anatomically adjusted with the ribs, and
   a geometry of the second extensions are anatomically adjusted with the manubrium.

4. The sternum implant according to claim 1, wherein the engineered polymers include PEEK, PEKK, or Carbon Fiber reinforced PEEK where fibers are continuous or discontinuous.

5. The sternum implant according to claim 1, wherein the sternum implant is custom developed for a patient with CAD/CAM techniques and computer-assisted surgical planning.

6. The sternum implant according to claim 1, wherein the sternum implant is manufactured by machining or additive manufacturing.

\* \* \* \* \*